(12) United States Patent
Granberry et al.

(10) Patent No.: US 12,209,336 B2
(45) Date of Patent: *Jan. 28, 2025

(54) ACTIVE KNIT COMPRESSION GARMENTS, DEVICES AND RELATED METHODS

(71) Applicant: Regents of the University of Minnesota, Minneapolis, MN (US)

(72) Inventors: Rachael Margaret Granberry, Saint Paul, MN (US); Kevin Eschen, Minneapolis, MN (US); Julianna Abel, Minneapolis, MN (US); Bradley Holschuh, North Oaks, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 277 days.

This patent is subject to a terminal disclaimer.

(21) Appl. No.: 17/652,392

(22) Filed: Feb. 24, 2022

(65) Prior Publication Data
US 2022/0175059 A1    Jun. 9, 2022

Related U.S. Application Data

(63) Continuation of application No. 16/035,963, filed on Jul. 16, 2018, now Pat. No. 11,280,031.

(60) Provisional application No. 62/697,789, filed on Jul. 13, 2018, provisional application No. 62/532,638, filed on Jul. 14, 2017.

(51) Int. Cl.
| | | |
|---|---|---|
| *D04B 1/26* | (2006.01) | |
| *A61F 7/02* | (2006.01) | |
| *A61H 1/00* | (2006.01) | |
| *A61H 11/00* | (2006.01) | |
| *D04B 1/18* | (2006.01) | |
| *A61F 13/08* | (2006.01) | |

(52) U.S. Cl.
CPC .............. *D04B 1/26* (2013.01); *A61F 7/02* (2013.01); *A61H 1/006* (2013.01); *A61H 11/00* (2013.01); *D04B 1/18* (2013.01); *D04B 1/265* (2013.01); *A61F 13/08* (2013.01); *A61H 2205/10* (2013.01); *D10B 2509/028* (2013.01)

(58) Field of Classification Search
CPC . D04B 9/52; D04B 9/50; D04B 1/265; D04B 1/18; D04B 1/26; D04B 9/46; D04B 7/32; A61F 13/08
See application file for complete search history.

(56) References Cited

U.S. PATENT DOCUMENTS

| | | | | |
|---|---|---|---|---|
| 5,997,465 A | * | 12/1999 | Savage | A61F 13/085 600/20 |
| 6,010,471 A | * | 1/2000 | Ben-Noon | A61F 13/0273 601/149 |
| 6,123,681 A | * | 9/2000 | Brown, III | A61L 15/42 601/152 |
| 7,491,185 B2 | * | 2/2009 | Couvillon, Jr. | A61H 31/005 601/149 |
| 10,702,014 B2 | * | 7/2020 | Stasey | A43B 3/34 |
| 2003/0125781 A1 | * | 7/2003 | Dohno | A63B 24/00 607/48 |

(Continued)

*Primary Examiner* — Danny Worrell
(74) *Attorney, Agent, or Firm* — Merchant & Gould P.C.

(57) ABSTRACT

Garments having active and passive knitted rows can provide desired levels of compression. Garments made of active and passive knitted rows can provide dynamic levels of compression with respect to both location and over time to address a variety of conditions.

10 Claims, 19 Drawing Sheets

(56) References Cited

U.S. PATENT DOCUMENTS

| | | | |
|---|---|---|---|
| 2006/0079824 A1* | 4/2006 | Munch-Fals | A61F 13/085 602/61 |
| 2006/0122544 A1* | 6/2006 | Ciluffo | A61B 5/015 601/79 |
| 2006/0186700 A1* | 8/2006 | Browne | B60J 7/04 296/187.01 |
| 2008/0184468 A1* | 8/2008 | Stanford | A62B 17/005 2/458 |
| 2009/0234265 A1* | 9/2009 | Reid, Jr. | A61H 9/0078 602/76 |
| 2010/0005568 A1* | 1/2010 | Smith | D02G 3/328 66/178 R |
| 2012/0116492 A1* | 5/2012 | Seibold | D02G 3/448 623/1.13 |
| 2015/0140886 A1* | 5/2015 | Kapsali | D03D 15/292 442/353 |
| 2016/0186366 A1* | 6/2016 | Mcmaster | D04B 1/24 28/143 |
| 2016/0309834 A1* | 10/2016 | Zwick | A43B 3/26 |
| 2016/0374886 A1* | 12/2016 | Wyatt | A61N 1/3603 601/18 |
| 2017/0247822 A1* | 8/2017 | Atmanspacher | D04B 1/26 |
| 2017/0252252 A1* | 9/2017 | Wyatt | A61H 7/007 |
| 2019/0017199 A1* | 1/2019 | Granberry | B32B 3/08 |

* cited by examiner

ACTIVE KNIT COMPRESSION GARMENTS, DEVICES AND RELATED METHODS

PRIORITY CLAIM

The present application is a Continuation of U.S. application Ser. No. 16/035,963, filed Jul. 16, 2018, which claims the benefit of U.S. Provisional Application No. 62/532,638 filed Jul. 14, 2017, and also claims the benefit of U.S. Provisional Application No. 62/697,789, filed Jul. 13, 2018, each of which is hereby fully incorporated herein by reference.

TECHNICAL FIELD

Embodiments relate to wearable devices that can produce compression in desired locations, patterns, and quantities of force for a variety of applications including promotion or inhibition of circulation, treatment of anxiety-related disorders, and support or structural assistance such as vertical loading.

BACKGROUND

Garments with compression features have been used for aesthetic reasons, for medical treatment, or for a combination of the two. Aesthetics can be a key factor in adoption of a garment by consumers or by a patient who would benefit from wearing a compression garment, as poor design leads to dissatisfaction and noncompliance. Even where no therapeutic level of compression is needed, "athleisure" clothing has become popular, including which garments that exhibit some compressive force and are made to be stylish, form fitting, or shaping, as well as comfortable. Examples include leggings or active footwear, for example.

Compression garments are worn articles of clothing that apply pressure to the body either through garment reduction (e.g., knit shapewear) or through inflation (e.g., a blood pressure cuff). Compression is an effective medical treatment for disorders ranging from varicose veins and lymphedema to orthostatic intolerance and deep vein thrombosis. Compression garments can promote or inhibit circulation, and they can be used in the treatment of anxiety related disorders or for support or structural assistance (e.g., structural loading).

Conventional compression garments for medical use rely upon either under-sized or inflatable compression technologies, whereas compression garments that are primarily intended for aesthetics are typically under-sized and exhibit some elasticity. Under-sized elastic garments are typically associated with a particular portion of a user's body, such as a calf or forearm. The cross-section of the garment when relaxed is smaller than the cross-section of the portion of the body. When applied, the garment stretches and exerts force as the elastic contracts back towards its relaxed size. Other types of non-elastic, undersized compression technologies include oversized garments that can be made undersized by reducing the garment circumference after the garment has been donned by adjustable mechanisms, such as lacing, buckles, hook and loop tape, or straps.

Under-sized garments apply a substantially constant pressure on the portion of the user's body at each particular point. Depending on the user's anatomy, however, the amount of pressure can vary along the length of the garment. Although under-sized garments can be designed to provide substantially uniform pressure (or a desired pressure gradient) to a typical person, variations in user anatomy can result in variation from the intended pressure profile for that garment.

Furthermore, the pressure profile created by a garment can vary based upon the way in which it is used. The cross-sections of various body parts change depending upon whether the person is seated, standing, or lying down. Therefore an under-sized garment, which typically cannot be resized or reshaped depending on the user's activity level or body position, may apply different levels of compression for users with different levels or types of activity.

SUMMARY

Garments made of active and passive knitted materials can provide desired levels of compression. Garments made of active and passive knitted rows can provide dynamic levels of compression with respect to both location and over time to address a variety of conditions.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
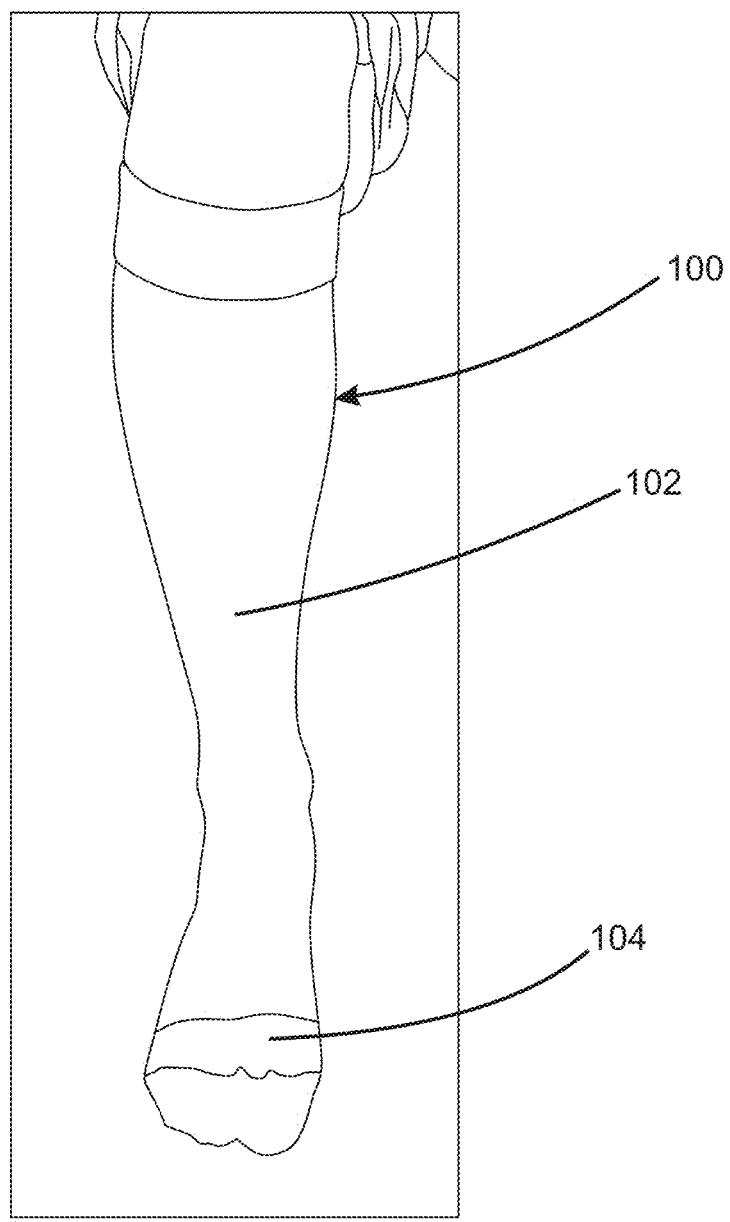
FIG. 1 depicts a passive fabric garment that is an under-sized compression garment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following disclosure describes several different garments, materials, and knitting patterns that can be used to produce therapeutic garments and aesthetically improved garments. Each of these garments is based on interconnected loops of shape memory alloy material, which can transition between a loose, flexible martensite state and an active, rigid austenite state. When loops of these material are knitted together they form a functional fabric that contracts upon activation.

Functional fabrics of all types described herein can provide actuation, sensing, energy harvesting, and communication as intrinsic fabric properties by integrating multifunctional fibers into designed textile geometries. The fiber material and the textile architecture can be designed to achieve functional fabric characteristics such as distributed actuation and sensing, variable stiffness, and complex, three-dimensional deformations. Through geometric design on the macroscopic and mesoscopic scales, knitted functional fabrics can achieve complex actuation deformations, such as corrugation, scrolling, and contraction. Additional, microscopic design parameters can be selected by the choice of multifunctional fiber and its specific material properties. Specific patterns and materials can be used to generate desired compression for either therapeutic, aesthetic, or other functional purposes such as the elimination of traditional fasteners that are required for non-compressive fabrics.

Throughout this disclosure, several specialized terms related to active knitted fabrics are used. The first is "knit index," which is the ratio of the area of a loop of active material enclosed in the martensite state and the square of the active knit material wire diameter. Depending on the knit index among other factors, a functional fabric with desired properties can be created. Two particularly important properties are the pressure applied by the fabric (i.e., how forcefully a garment made of the active fabric squeezes when the active material is actuated) and the actuation contraction of the fabric (i.e., the distance in total length of the fabric when the active material is actuated). Actuation contraction of an active knit fabric is a function of the martensite length $l_M$ and the austenite length $l_A$:

$$\zeta = (l_M - l_A)/l_M.$$

Depending on the knit index, the diameter of the active material, and other factors, different types of active fabrics can be created. One type of fabric is referred to herein as a "therapeutic compression garment," and it is designed primarily to provide a therapeutic level of compression to a wearer. Accordingly, the level of force applied by the fabric when activated should preferably reach a desired minimum level, while the total actuation contraction is of lesser importance.

A second type is referred to as a "self-fitting" garment, which is not intended to provide therapeutic compression but rather to contract to a accurate fit for the wearer. Accordingly, the level of force applied by the garment should be smaller than that of a therapeutic compression garment, while the total displacement should be larger.

Other garments, fabrics, or portions thereof can be made of "passive" material, which refers to materials that do not exhibit a shape-memory transition.

Passive Fabric Compression Garments

Figure 2:
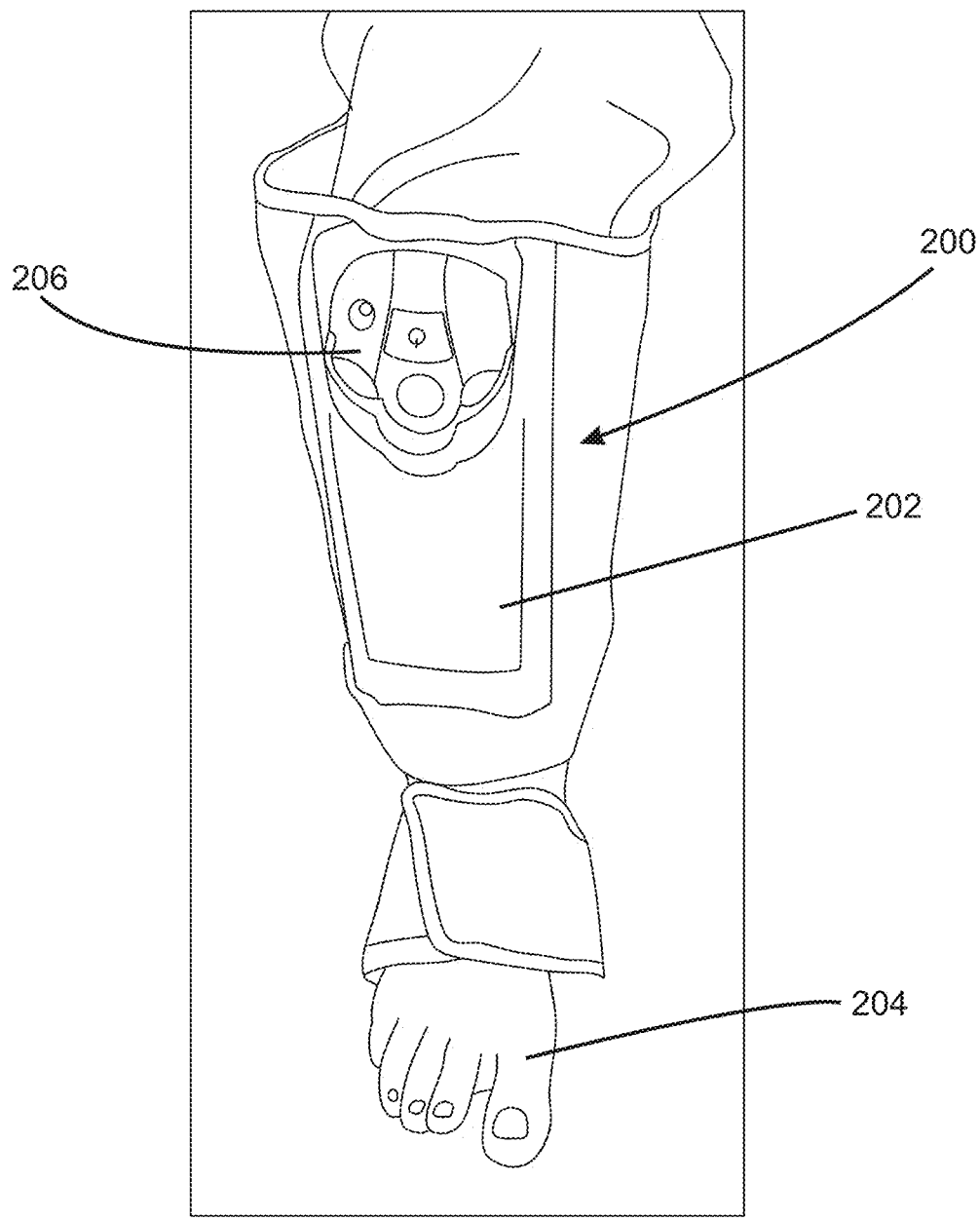
FIG. 2 depicts a passive fabric garment that is a pneumatic compression garment.

FIGS. 1 and 2 relate to prior passive and active compression garment technologies.

FIG. 1 shows an under-sized compression garment 100 applied to a user's calf 102 and foot 104. When donned, under-sized compression garment 100 applies pressure on calf 102 and foot 104 based upon the amount garment 100 is stretched. As shown in FIG. 1, under-sized garment 100 is tubular in shape, with a circumference that varies along its length. Typically, under-sized garment 100 has an unstretched circumference that is smaller than a body part that it is used with. Therefore in order to don the garment 100, it is necessary to pre-stretch the garment 100. In more complex garments, pre-stretching the garment becomes more burdensome. For example, some garments are worn on parts of the body that are smaller than the area they must pass over to be donned. In one example, a shirt must be stretched to pass over a user's head, even though the garment should preferably ultimately be sized to fit on a smaller region such as around the neck. In another example, a pair of pants includes a portion that is worn around the user's ankles or calves, but the entire garment must be stretchable to fit over the user's foot, which has a much larger cross-section.

Thus conventional under-sized garments relying solely on elasticity to provide desired compression must overcome several obstacles in order to be useful. The tension properties or stiffness of the elastane must be high enough to provide the desired compression while still remaining loose enough that the garment can be stretched during donning or doffing of the garment. Elongation of a passive knit material has been studied, and is typically measured after pretensioning with a low amount of force, such as 0.5N. In order to achieve this goal, conventional compression garments can incorporate high-elongation fabrics as well as any of a number of fasteners such as zippers, snaps, or ties that can be fastened after the garment has been positioned on the user's body to increase the compression on a desired region.

FIG. 2 shows a pneumatic garment 200 applied to a user's calf 202 and a portion of the user's foot 204. Pneumatic garment 200 is significantly bulkier than under-sized compression garment 100 of FIG. 1. Pneumatic garment 200 is capable of providing controlled and variable amounts of pressure, unlike under-sized compression garment 100 of FIG. 1. Pneumatic garment 200 of FIG. 2 includes a set of controls 206 that can be manipulated to increase or decrease the applied pressure. By pumping air into pneumatic garment 200, the thickness of the garment is increased and pressure on the calf 202 and/or foot 204 is increased.

Unlike under-sized compression garment 100, pneumatic garment 200 is capable of increasing or decreasing pressure during use. Pneumatic garment 200 also adjusts somewhat for changes in circumference of the body part that can result from sitting, standing, lying down, or other movements or changes in position. Pneumatic garment 200 is substantially heavier and bulkier than under-sized compression garment 100, as it includes controls 206 and associated pumps, valves, sensors, and power storage such as a battery necessary to transfer and hold air at above-atmospheric pressure.

Therapeutic Compression Garments

FIGS. 3-8 relate to therapeutic compression garments.

Figure 3:
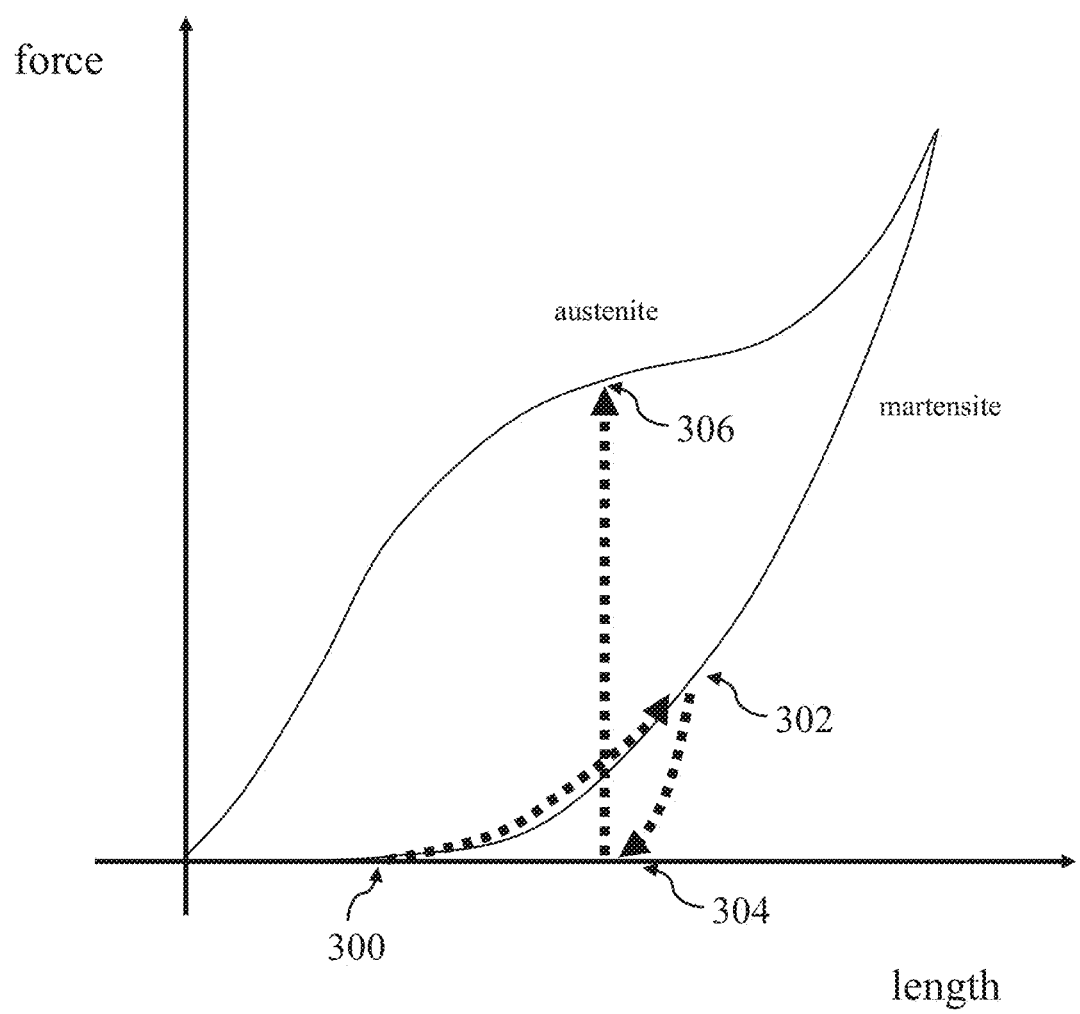
FIG. 3 is a force-length diagram for a therapeutic compression garment according to an embodiment.

FIG. 3 is a chart of a theoretical model for the force and length of a therapeutic compression garment. Force applied to the fabric or garment, shown on the y axis, can be used to determine a total tension using a tensile test that measures a fabric's tension (T) at specific lengths, $$T = F/w$$

where the recorded force (F) is divided by the measured fabric width (w). By determining the tension values of the fabric, the pressure exerted by the fabric on a body can be determined for specific fabric lengths. In one example, an orthostatic intolerance lower body garment exerts between about 6 mmHg and about 77 mm Hg (about 800 Pa and about 12 kPa) on the body. The range of fabric tensions required for this garment can be determined using the Hoop Stress formula, Laplace's formula, and Macintyre's formula:

Hoop Stress formula:

$$\delta_\theta = F/tw$$

where $\delta_\theta$=hoop stress, F=force in N, t=fabric thickness in m, w=fabric width in meters.

Laplace's formula:

$$P = (t\delta_\theta)/r$$

where P=pressure in Pa, t=fabric thickness in m, $\delta_\theta$=hoop stress, r=limb radius in meters.

Macintyre's modified formula:

$$P = (t(F/tw))/r,$$

i.e., P=(F/w)/r, because T=F/w and the t's cancel out;
i.e., P=T/r where P=pressure in Pa, T=fabric tension in N/m, r=limb radius in meters.

Anthropometric data can be gathered to determine the limb radius. The anthropometric data can be specific to a patient, or in embodiments standard or common sizes can be used to generate garments that are appropriate for many wearers. In this example, if the average leg radius is 0.049 meters, Lowest pressure:

$$799.9 \text{ Pa} = \frac{T}{0.049 \text{ m}},$$

then T=799.9 Pa*0.049 m, then T=39 N/m

Highest pressure:

$$10265.8 \text{ Pa} = \frac{T}{0.049 \text{ m}},$$

then T=10265.8 Pa*0.049 m, then T=503 N/m.

So to provide the desired level of compression, the fabric should exhibit tensions levels between 39 and 503 N/m.

Returning to FIG. 3, at 300 the therapeutic garment is an undersized garment in the martensite state. No force is being applied by or to the garment. At 302, some force is applied to the garment to stretch it over the user. The garment remains in the unactivated martensite state, so the length of the garment increases along the bottom curve in FIG. 3 as force is applied to stretch the garment.

Once the garment is donned, the garment relaxes as shown at 304, and force applied returns to about zero while length is somewhat greater than the original length at 300. This is different from passive garments such as the elastic garment shown in FIG. 1, which maintain some non-zero force on the wearer at all times upon being stretched.

At 306, the fabric that makes up the garment is actuated, such as by application of heat. This actuation, or transition from martensite to austenite phase, causes an increase in applied force (i.e., compression), even though there is little to no change in the length of the fabric. The garment size enters a "blocked state" in which it cannot move, but force increases.

The garment can be changed back to martensite to be removed, or in embodiments the state of the fabric can be alternated between austenite and martensite to provide pressure pulses or other therapy, as described in more detail below.

Figure 4A:
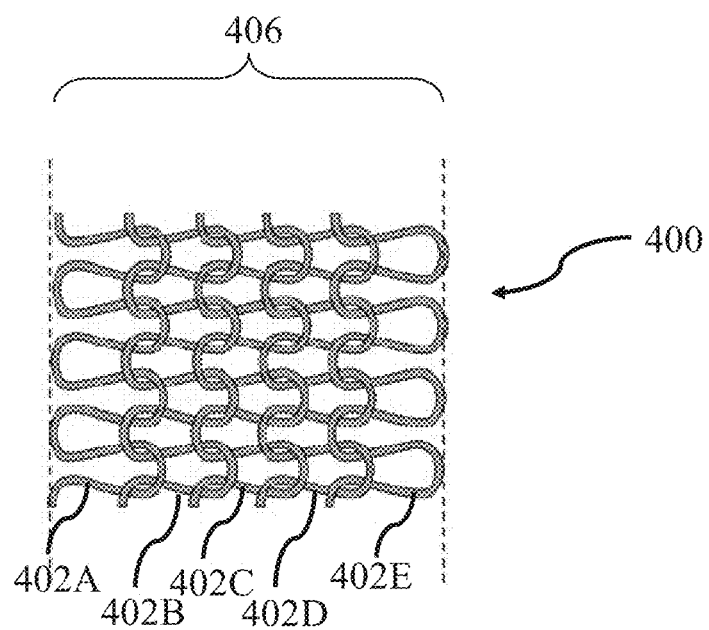
FIGS. 4A and 4B are plan views of the fabric for a therapeutic compression garment with weft knit active yarns in relaxed and contracted states, respectively, according to an embodiment.
Figure 4B:
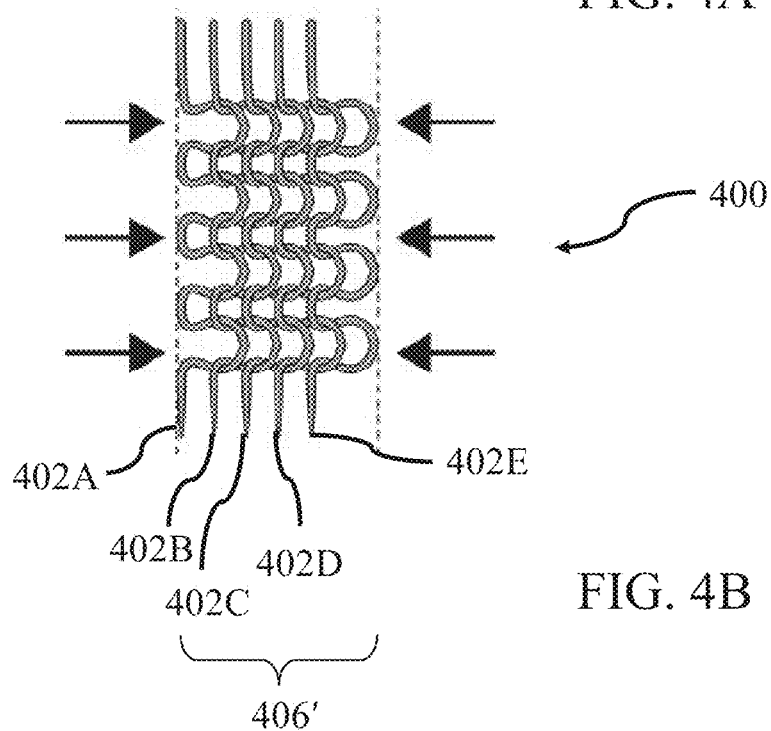

FIGS. 4A and 4B are plan views of fabric 400 made of a series of rows of weft knit active yarns in relaxed and contracted states, respectively, according to an embodiment. Fabric 400 includes five rows (402A, 402B, 402C, 402D, 402E) of an active yarn material. The term "active yarn material" can refer to any thread, strand, filament, braid, or bundle of materials that responds to thermal or electrical stimulation to change from a relaxed state to an activated state. In embodiments, braided or coaxial bundles can provide a relatively higher level of strength than individual filaments and can also provide more force when switching between relaxed and activated states.

The active yarn material that makes up each of the rows 402A, 402B, 402C, 402D, 402E can comprise a shape memory alloy (SMA). In embodiments, the SMA can be a type of active metal with pseudoelastic properties that is highly malleable in a cool, martensite phase and has shape recovery abilities, even under load, during the elastic austenite phase. In one embodiment, the active yarn material can be a nitinol material. SMAs can be engineered to switch from martensite to austenite depending on whether they are above or below a transition temperature.

SMAs can be engineered to exhibit desired properties by altering the material composition and the heat treatments. Specifically, stress, strain, recovery, and activation temperature are functional properties that can be manipulated through the thermomechanical manufacturing process. Consequently, SMAs can be designed to activate at specific temperatures to require relatively low power consumption and temperature loads on the body compared to powered, pneumatic systems.

Knit structures such as fabric 400 can be used in large, complex structures that are actuated across complex surfaces (such as the surface of the body). The variety of structures that can be created with interlocking loops or stitches within each row (e.g., rows 402A, 402B, 402C, 402D, 402E) and the shape change that occurs when these loops are subject to tension can be customized to the contours of a particular body part such as a leg or arm.

Knitting can be divided into two general architectures: (1) weft knitting, which is a process in which an individual end of yarn is fed into or knit by one or more needles in a crosswise (lateral) fashion, and (2) warp knitting, which is a process in which a multiplicity of yarns are fed into or knit by one or more needles in a lengthwise (vertical) fashion. While weft knits have more mechanical stretch, warp knits are often more stable architectures and can be constructed using many wales, or columns, of yarn. Additional yarns can be introduced into weft knit structure by utilizing a jacquard system, which selectively engages and disengages needle beds to form a knit pattern using multiple yarns. Warp knits can also achieve complex patterning through the use of guide bars, which allow some warp knit structures (e.g., raschel knits) to appear like lace-structures. Hand-knitting (a weft knit structure), lace-making, crocheting, tadding, and needle-lace are other manual methods of selectively looping yarns into a fabric structure. Complex patterns can be achieved using other techniques such as hand-knitting, lace-making techniques, or others, which can be used to loop yarns selectively into the fabric structure. Although FIGS. 4A and 4B depict a simple weft pattern, other embodiments can include a variety of relatively more complex knitting stitches and patterns including warp knitting, jacquard, intarsia, Fair Isle, or any other knitting pattern and combinations thereof.

FIG. 4B shows the same five rows 402A, 402B, 402C, 402D, 402E of active material described above with respect to FIG. 4A, but in FIG. 4B the rows 402A, 402B, 402C, 402D, 402E are in a compressed state indicated by arrows. Fabric 400 can change from the relaxed state shown in FIG. 4A to the compressed state shown in FIG. 4B due to a change in temperature. For example, the active material can have a transition temperature, and once each of the rows 402A, 402B, 402C, 402D, 402E becomes hotter than that transition temperature the active material can transition from martensite to austenite, and vice versa.

As shown in FIGS. 4A and 4B, depending upon the state of the rows of an active material, the overall width of the fabric can vary. Width of an active fabric can be relatively wider in the relaxed state, and relatively narrower in the activated state. A user can change between these two states by heating or cooling the rows. To heat the rows, electrical current can be routed through some or all of the rows. Alternatively, an adjacent liner can provide heat or cooling to fabric to cause it to change between activated and relaxed states.

A fabric made of a shape memory alloy or other active knit material can be modified to form other fabric types or patterns by changing any of at least five features. First, the relative number of active yarns to passive yarns (as described in more detail below with respect to FIGS. 5A-5C) can be varied to provide different levels and targeted areas of compression. Second, the stitch size or relative density (i.e., gauge) of the stitches can be modified to affect the knit index $i_k$. Third, current and voltage (or power dissipation) through the active yarns can be controlled to affect activation of each of the active yarns. Fourth, the weight or diameter of the yarn (which can be either a single filament or a bundle of active filaments) can be modified, with thicker yarns generally providing a higher level of compression upon activation. Finally, the transition temperature of the active yarns can vary between embodiments, and in fact within segments of the same fabric, to create zones as described in more detail below. Zones that have different transition temperatures will activate at different times, even under uniform heating or cooling.

Figures 5A, 5B:
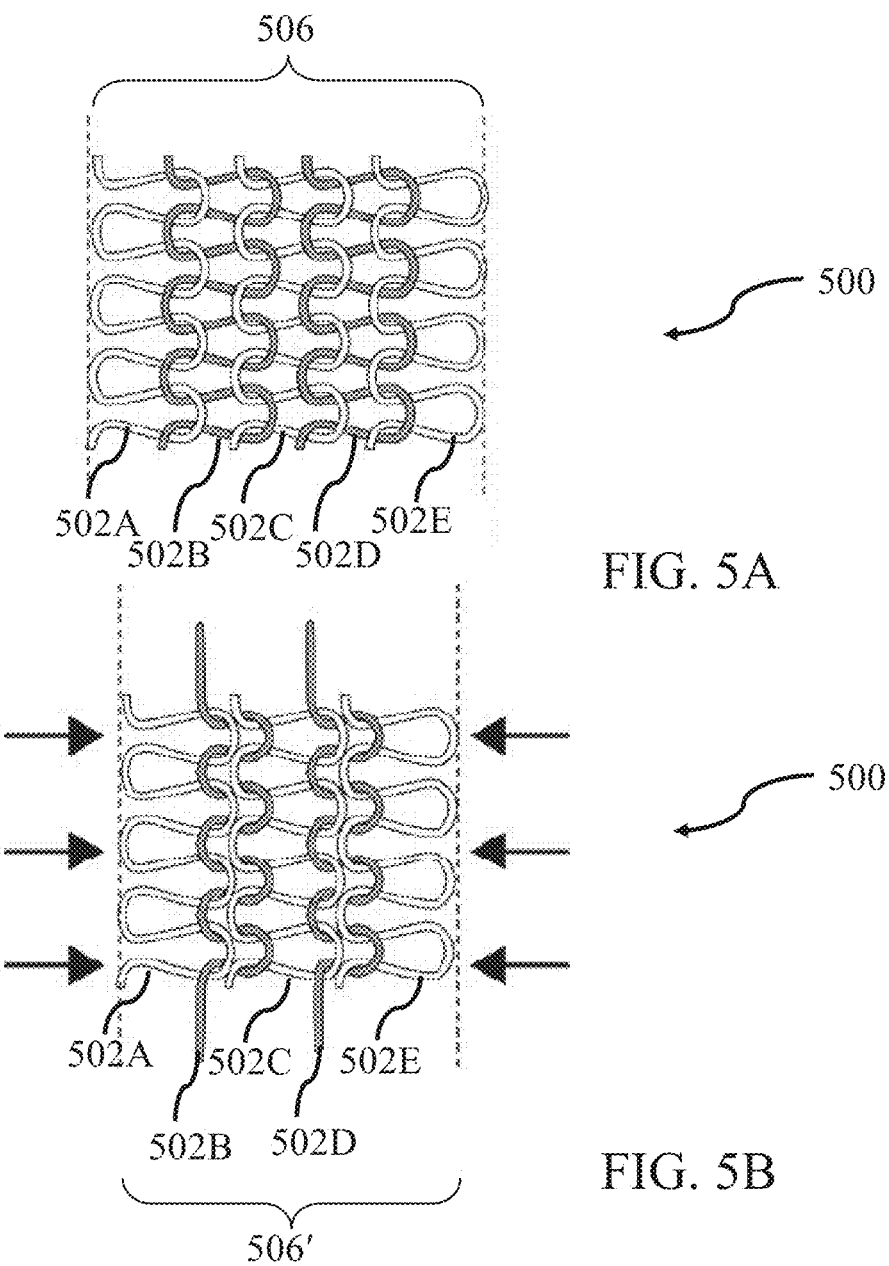
FIGS. 5A and 5B are plan views of the fabric for a therapeutic compression garment with weft knit active and passive yarns in relaxed and activated states according to an embodiment.

FIGS. 5A and 5B are plan views of fabric 500. Fabric 500, like fabric 400 of FIGS. 4A and 4B, includes five rows (502A, 502B, 502C, 502D, 502E) of knitted material. Fabric 500, unlike fabric 400, includes multiple knitted materials in alternating rows. Shaded rows 502B and 502D are an active yarn material, similar to the material that makes up active rows 402A-402E described above with respect to FIGS. 4A and 4B. In contrast, rows 502A, 502C, and 502E are made of a passive material that does not transition between martensite and austenite states. A passive material can be non-conductive such that electrical heating will not occur in a passive material. For example, the passive material could be a non-conductive polymer. A non-conductive polymer will not draw power when a voltage source is attached to it, therefore use of passive zones in a fabric (e.g., fabric 500) can reduce overall power dissipation per unit area.

Consequently, while in the relaxed state fabric 400 of FIG. 4A looks substantially the same as fabric 500 of FIG. 5A. In contrast, in the activated state fabric 400 (shown in FIG. 4B) compresses by a greater amount than fabric 500 (shown in FIG. 5B, compression indicated by arrows). That is, the proportional difference between width 406 and width 406' is larger than the difference between width 506 and width 506'.

Figure 6A:
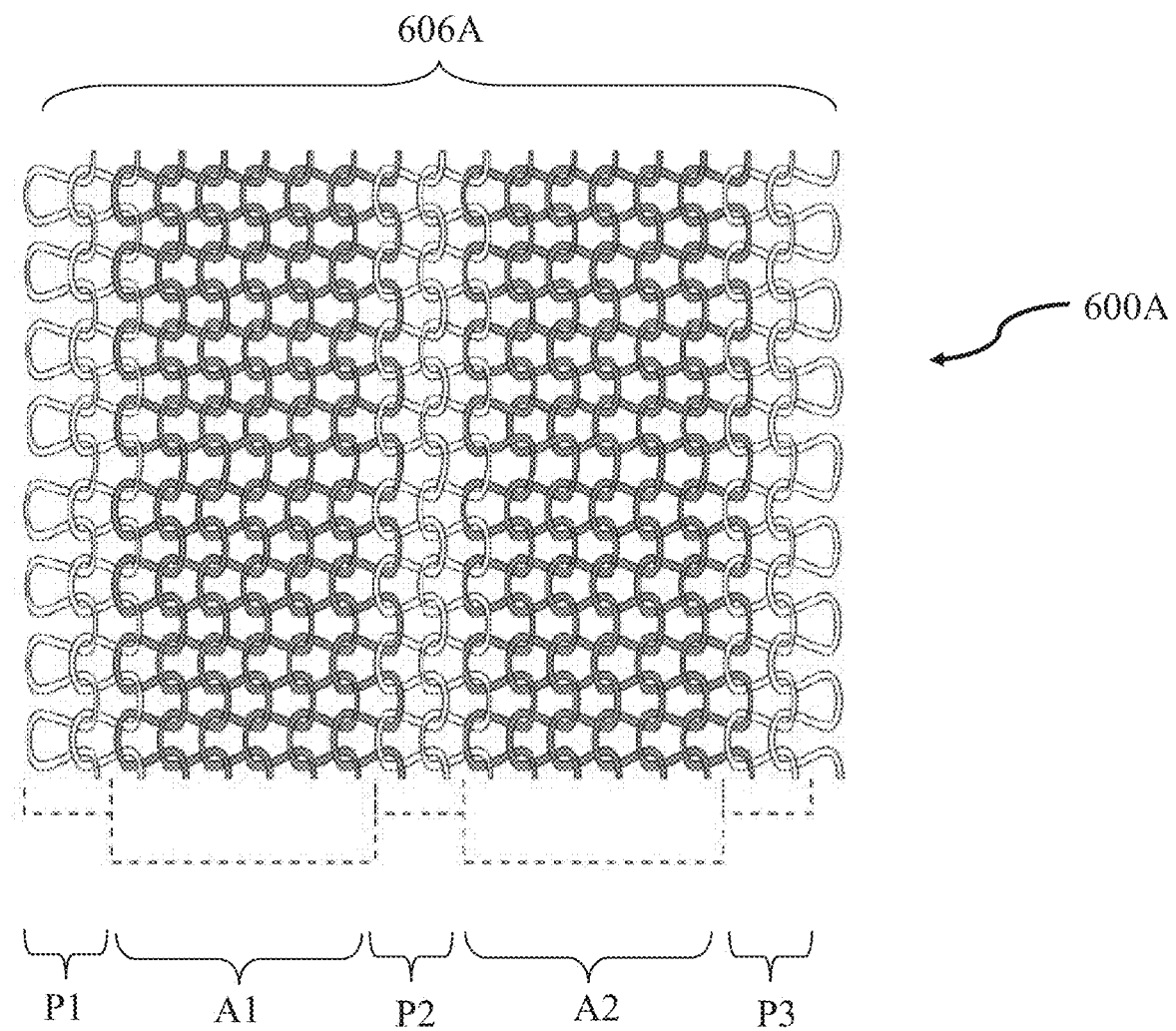
FIGS. 6A-6C are plan views of the fabric for a therapeutic compression garment with fabric segments having active and passive sections according to three embodiments.
Figure 6B:
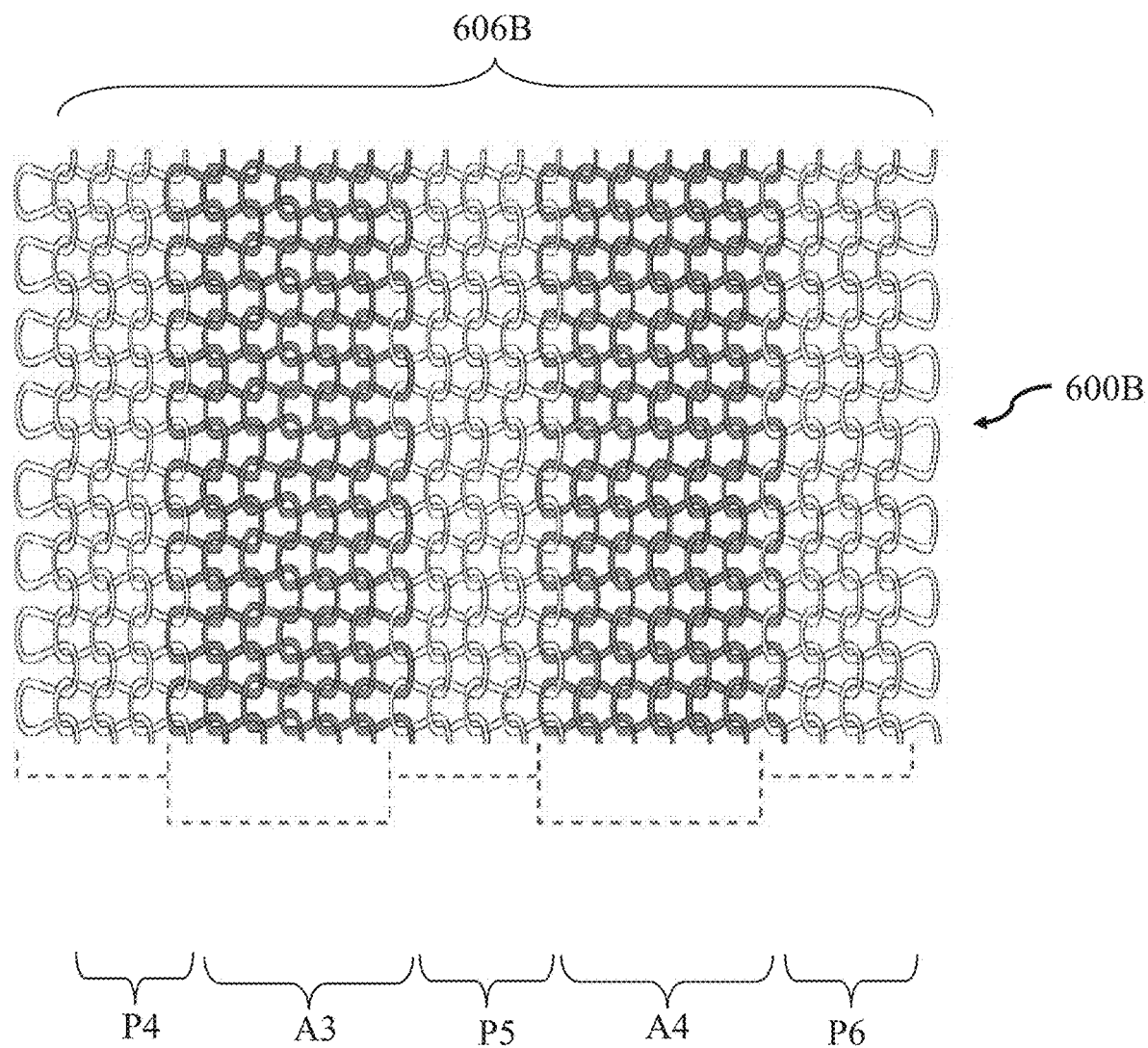
Figure 6C:
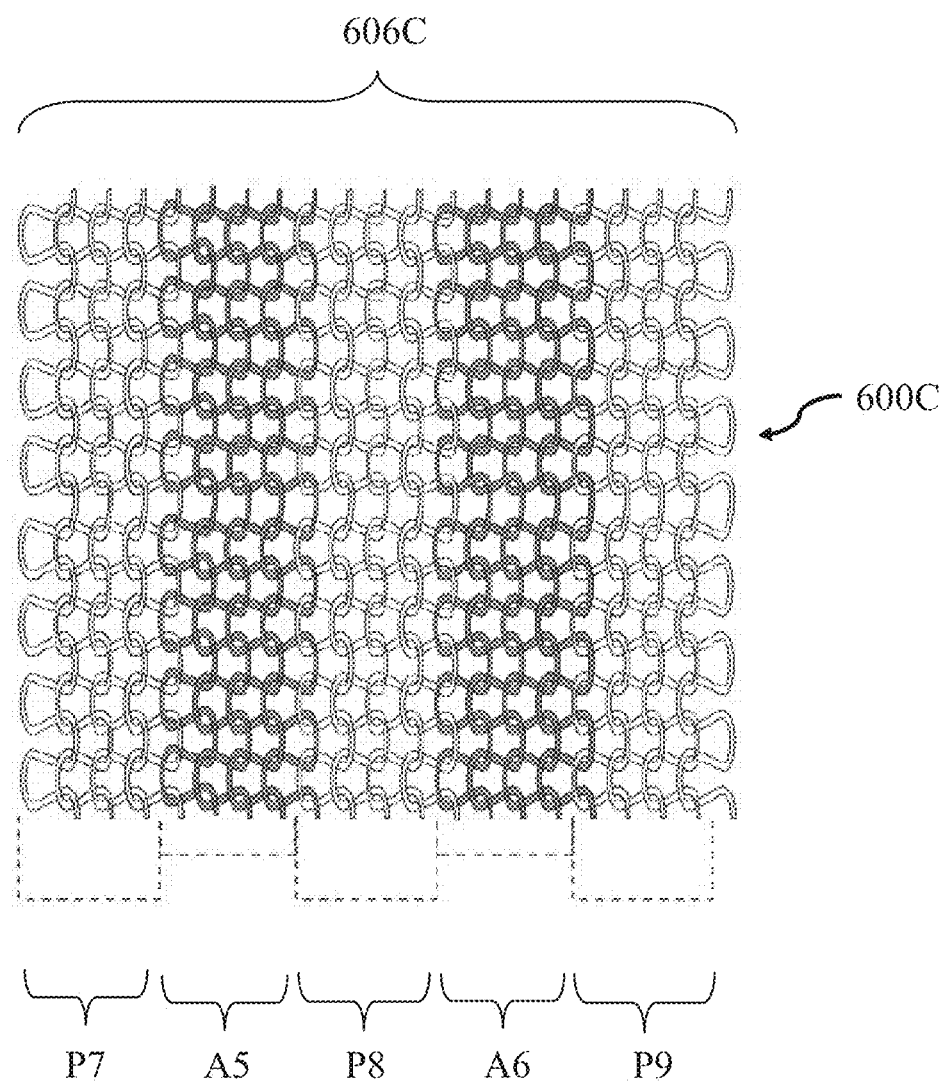

FIGS. 6A, 6B, and 6C are plan views of three weft knitting patterns including active and passive sections.

As shown in FIG. 6A, fabric 600A includes two active sections A1 and A2, as well as three passive sections P1, P2, and P3. Active sections A1 and A2 are each made up of six rows of active knitted material, described above with respect to FIGS. 4A, 4B, 5A, and 5B. Fabric 600 is shown in the relaxed state. By applying heat to active section A1 and/or active section A2, the width 606A of fabric 600A can be reduced.

The maximum possible extent of the reduction in width varies based upon the number of rows of knitted material within each active section (A1, A2) and the number of rows within each passive section (P1, P2, P3), in addition to the factors described above ($i_k$ and d) that affect actuation contraction. Likewise, the maximum possible pressure depends on the applied force $F_{app}$ as described above. For a therapeutic compression garment, the applied force is often relatively high while the total actuation contraction is low, which can be facilitated by the use of passive sections P1-P3 interspersed with active sections A1 and A2 that provide strong contraction over a short distance.

In the embodiment shown in FIG. 6A, each active section A1, A2 includes six rows, whereas each passive section P1, P2, P3 includes two rows of passive material. Therefore 75% of the rows within fabric 600A can be activated to cause compression. In alternative embodiments such as those shown in FIGS. 6B and 6C, where different portions of the fabric are active or passive, the length can remain constant in passive regions while varying due to activation of the active regions as described in the equations above.

Active sections A1 and A2 can be activated independently of one another. For example, in embodiments fabric 600A can be activated by applying an electrical current through active sections A1 and A2 to cause heating. In some cases it may be desirable to activate less than the full 75% of the rows. For example, if it is desirable to activate only 37.5% of the rows, either active section A1 or active section A2 could be activated, leaving the other in the passive state.

FIG. 6B is an alternative embodiment in which fabric 600B includes active sections A3 and A4, as well as passive sections P4, P5, and P6. Like fabric 600A, fabric 600B includes active sections A3 and A4 that each include six rows of an active or shape-memory material. Fabric 600B has relatively wider passive sections P4, P5, and P6 than the counterpart passive sections P1, P2, and P3 of FIG. 6A. In particular, passive sections P4, P5, and P6 each have four rows, in contrast to the 2-row passive sections P1, P2, and P3 of FIG. 6A. The percentage of rows that are active in fabric 600B of FIG. 6B is therefore 60%, compared to 75% that are active in fabric 600A of FIG. 6A.

FIG. 6C is an alternative embodiment in which fabric 600C includes active sections A5 and A6, as well as passive sections P7, P8, and P9. Active sections A5 and A6 each include four rows of an active or shape-memory material, while passive sections P7, P8, and P9 each include four rows of a passive material. The percentage of rows that are active in fabric 500C of FIG. 7C is therefore 50%, compared to 75% that are active in fabric 700A of FIG. 6A or 60% in fabric 600B of FIG. 6B.

Figure 7A:
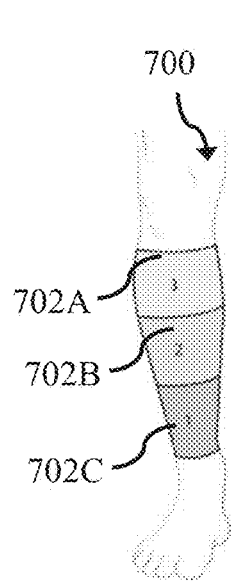
FIGS. 7A-7C are front, back, and side perspective views, respectively, of a therapeutic compression garment according to an embodiment.
Figure 7B:
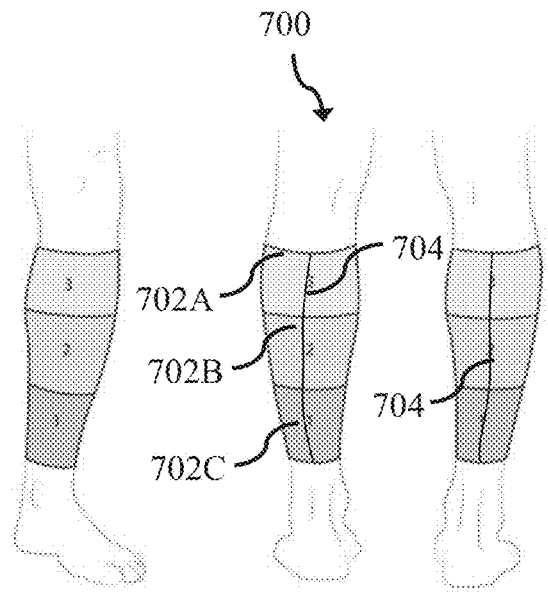
Figure 7C:
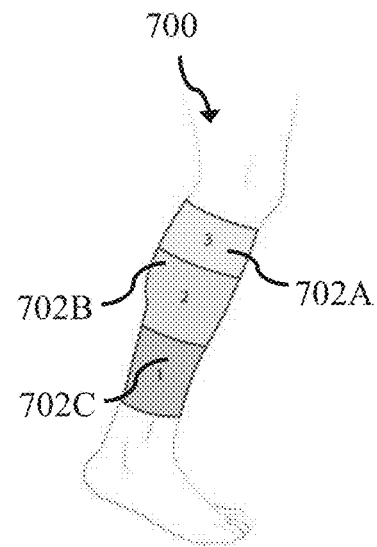

FIGS. 7A, 7B, and 7C are front, back, and side perspective views of a therapeutic compression garment 800 according to an embodiment. Therapeutic compression garment 700 includes three sections, 702A, 702B, and 702C. Each of the sections 702A-702C is made up of a different composition of active and passive material. Therefore the level of compression in each section 702A-702C is different, because each section 702A-702C will contract by a different amount when the active sections therein are activated. Compression levels can be targeted to areas where it desirable to apply relatively higher or lower amounts of compression. The different compositions in each section can be, for example, different knit tightness or pattern (affecting $i_k$), different diameter of knit material (affecting d), different ratios of active to passive materials, or the use of different materials that have different shape memory characteristics such as transition temperature, transition displacement, or transition force.

FIG. 7B shows connector 704. In embodiments, connector 704 can be a zipper, a pair of hook-and-loop connectors, snaps, buttons, or other fasteners to couple the edge of garment 700 to another edge or portion of garment 700 to form a closed loop or sleeve. In alternative embodiments, connector 704 may not be required. Depending on the size of the loops that make up each of the active and passive rows, as well as the thickness of the material, some embodiments of garment 700 are loose enough to be donned without a connector 8. Such embodiments can be permanently sewn together, or other techniques such as knitting-in-the-round can be used to create those embodiments.

In alternate embodiments, the sections 702A-702C can have equal percentages of active and passive material, but the sections 702A-702C can be operated differently. For example, half of the active sections of one zone may be activated, while three quarters of the active zones of another zone are activated, and all of the active zones of the third zone are activated. Compression gradients can be created in this way without customizing the knitting pattern of the garment.

In alternate embodiments, zones need not be circular and extend longitudinally. Instead, zones could be arranged at different azimuthal positions within a cylindrical section, or zones could be any other irregular shape that can be knitted into the overall fabric. Active sections can be concentrated in areas where compression is desired, as higher concentrations of active regions can be used to focus the compression to those areas.

Figure 7D:
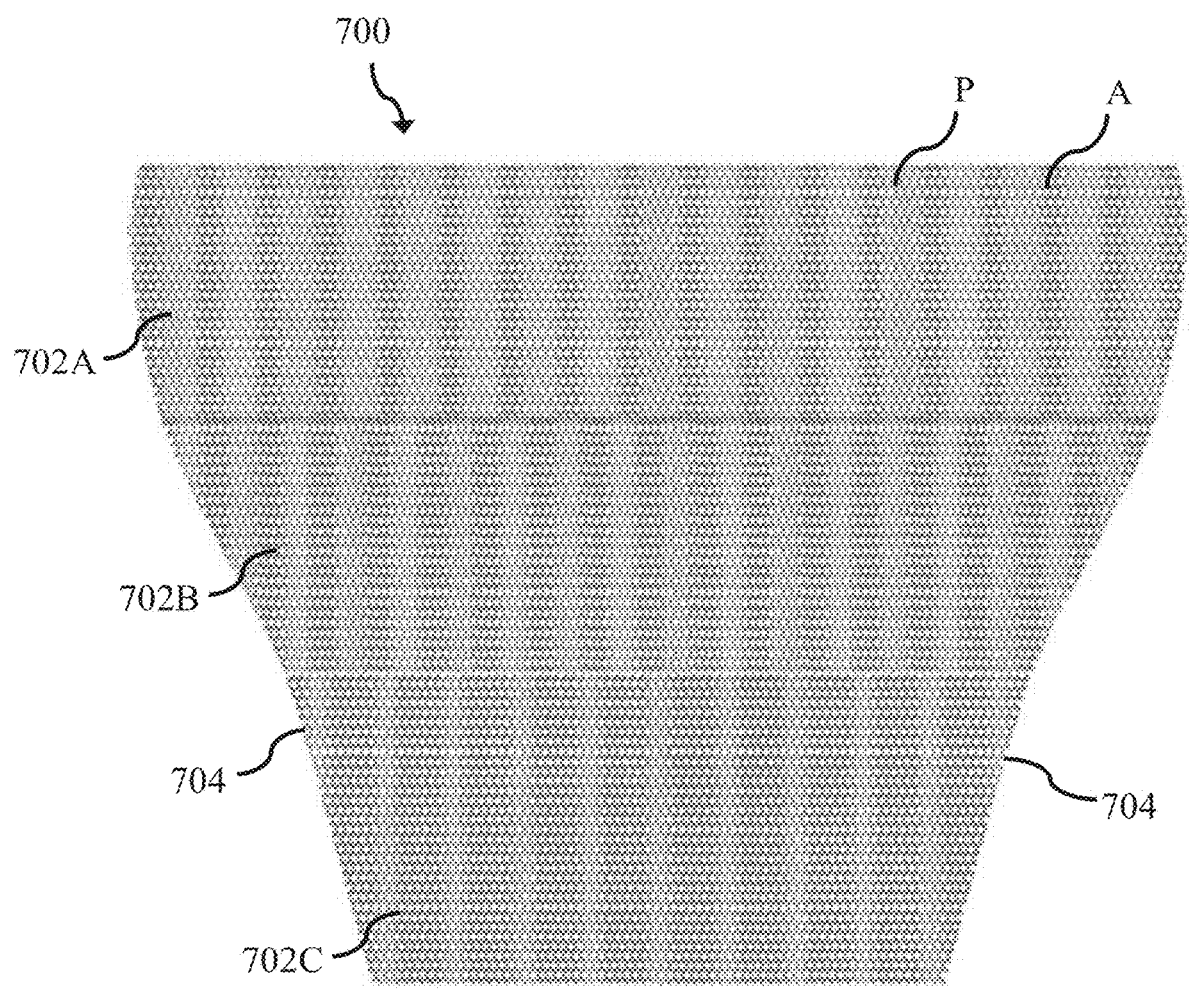
FIG. 7D is a plan view of the garment of FIGS. 7A-7C.

FIG. 7D is a plan view of garment 700, laid out flat with connector 704 disconnected. As shown in FIG. 7D, zone 702A has a relatively high percentage of passive sections P (shown in light color), zone 702B has a slightly lower percentage of passive sections P, and zone 702C has the lowest percentage of passive sections P (and, correspondingly, the highest percentage of active sections A).

Other garments can be configured to adapt compression levels based on the body's dynamic shape change. For example, a garment with an active material architecture can be designed to dynamically expand in circumference from 1 to 6% at the calf and from 1 to 8% at the ankle when the wearer transitions from a standing to a seating posture to accommodate anthropometric changes and maintain a target pressure output. A garment for use on a knee region can take into account increasing radii to prevent tourniquetting of blood into the feet and calves. An active architecture can expand up to 7% at the knee when sitting, in an embodiment, up to 12% in other embodiments, or up to 13% in alternative embodiments. For thigh compression, the active material architecture can expand or contract from a target standing circumference. To accommodate the anthropometric requirement of the thigh, an active material designed for the thigh region can have a greater circumferential stroke change than other regions of the leg. Like the knee, the thigh region requires the design of several different active architectures according to weight category. In some embodiments, the total amount of compression can correspond to a circumferential change up to 14% in some embodiments, up to 15% in other embodiments, up to 16% in still further embodiments, and up to 17% in still further embodiments. In other embodiments, tourniquetting of the blood can be desirable, and therefore the amount of compression applied to a particular region may exceed the amount that permits normal blood flow.

Active materials can be selected that have transition temperatures near the ambient temperature of areas where they will be used. For example, compression garments could have active zones knitted from an active material that has a transition temperature slightly higher than skin temperature. Very little additional energy is then required to cause the material to change to the activated state, and no energy is required to cool the active material back below its activation temperature. Transition between states can also be rapid as the total amount of temperature change required to transfer between the states is small.

In embodiments, the level of compression provided by a garment or even a particular zone within a garment can vary over time. For example, power can be supplied to active materials to cause heating and activation, then power can be stopped and the material allowed to cool, at a desired frequency. Entire zones can be pulsed in this way, and pulsing of different zones can be coordinated. Coordination of pulsed pressure application can be used, for example, to promote lymph flow or blood circulation. In embodiments, sensors can be used to detect attributes of the patient. For example, sensors can detect a pulse rate of a patient, and pulsing of the power supply can correspond to that pulse rate in order to promote circulation. A control system, either with or without sensors, can be used to set the pulse rate, compression amount, or other aspects of the garment.

In embodiments where more rapid pulsing is required, or where the activation temperature of the active material is close to the ambient conditions where that garment will be used, active cooling can be employed to more rapidly convert the material back to its relaxed state. For example, a sleeve can surround the active material in a garment, and the sleeve can act either as a heat sink or can be actively chilled.

Other sleeves and liners that promote comfort or ease of use of the garment can be used. In one embodiment, an inner sleeve of a smooth material is attached to the active and passive material zones. The inner sleeve acts as a barrier to prevent contact of the fabric (e.g., fabric 400, 500) with the user. Inner and outer sleeves or liners can include medicaments or other substances, in embodiments.

Figure 8:
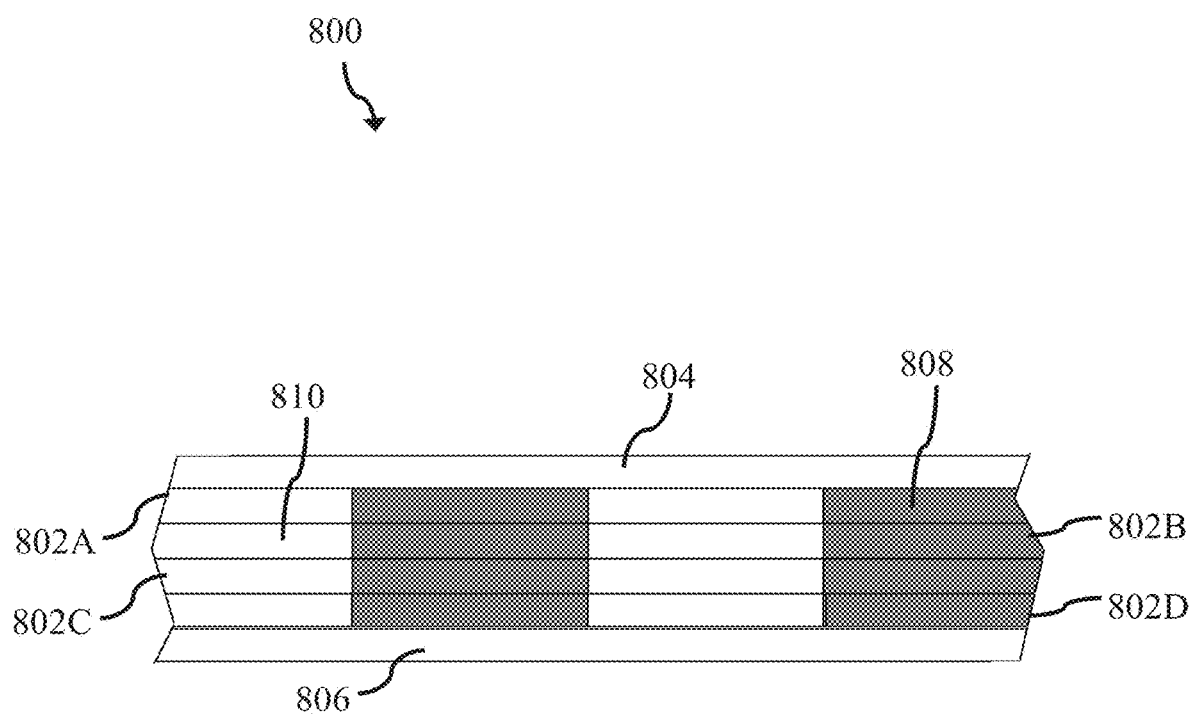
FIG. 8 is a cross-sectional view of a portion of a multi-layer therapeutic compression garment according to an embodiment.

As shown in FIG. 8, a multi-layer garment 800 can include four separate compression layers 802A, 802B, 802C, and 802D, arranged between a top liner 804 and a bottom liner 806. Each compression layer 802A-802D is made up of active material 808 and passive material 810. Active material 808 and passive material 810 can be knitted together as described above. Multiple layers 802A-802D can be used to generate more compressive force than a single layer, which can be beneficial depending upon the compressive strength of the active material 808 and the amount of compression desired.

Figure 9:
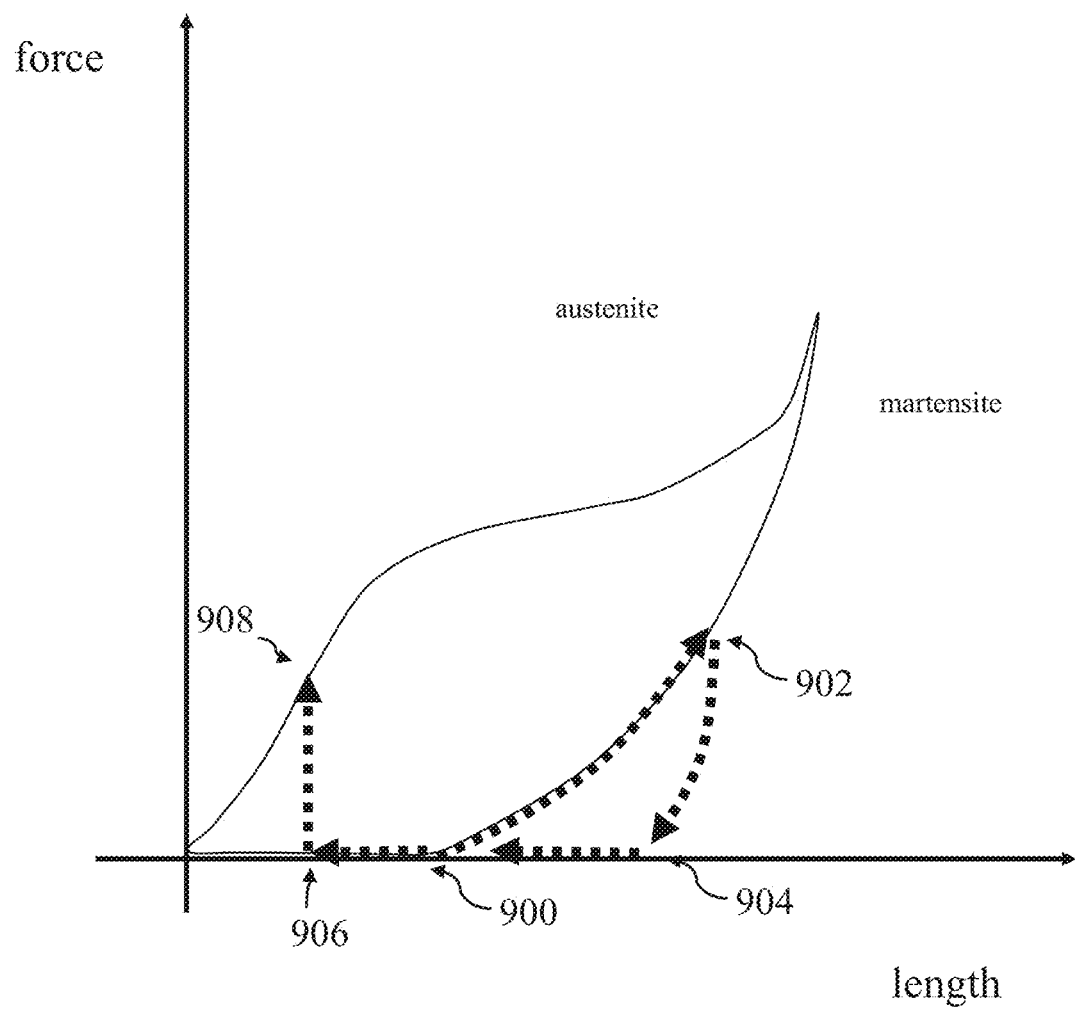
FIG. 9 is a force-length diagram for a self-fitting garment according to an embodiment.

In embodiments, top liner 804 can be connected to the closest compression layer 802A. The connection can be either continuous (i.e., interwoven), or in embodiments top liner 804 can be loosely connected to compression layer 802A. Likewise, bottom liner 806 can be either tightly or loosely coupled to compression layer 802D. In alternative embodiments, active regions 808 or each layer (802A, 802B, 802C, 802D) need not align with one another in regular columns as shown in FIG. 9. Rather, the active regions 808 could be staggered, or could be sized and positioned differently between each of the layers (802A, 802B, 802C, 802D).

Self-Fitting Garments

FIGS. 9-15B relate to self-fitting garments.

Self-fitting garments rely on the same underlying principles of transition from martensite to austenite and back that are described above with respect to therapeutic compression garments. In self-fitting garments, however, the goal is often to have the garment shrink to size for a wearer, without applying any constrictive force.

As described above, in knitted active materials a relevant parameter that affects the overall compression provided by a knitted segment is defined by the ratio of the loop area enclosed in the martensite state ($A_{l,m}$) and the square of the active knit material wire diameter d:

$$i_k = A_{l,m}/d^2.$$

It should be understood that in embodiments it may be desirable to use a thread or yarn of active materials, or a twisted pair or trio of wires, or any of a variety of braids, for example, and the equations herein apply to the idealized case. Each alternative configuration will have different compression characteristics, which are not described in detail within this disclosure.

In the idealized case of knit material with circular cross sections, the knit index $i_k$ is an intuitive and easily obtainable parameter describing the dimensionality of contractile SMA knitted actuators. A low knit index corresponds to densely knitted fabrics, with a relatively high proportion of active material in a unit area.

FIG. 9 is similar to FIG. 3 in that it shows force and length for an active fabric. Unlike FIG. 3, though, FIG. 9 depicts the change in length and force for a self-fitting garment. In general, as described above, self-fitting garments aim to provide more displacement and less force, to provide a garment with little or no "ease" (i.e., little or no difference in circumference of the garment compared to the circumference of the body part it covers).

At 900, an oversized, martensite garment is provided. As the garment is donned at 902, some force is applied to stretch the garment. Once donned, the martensite garment relaxes on the body, such that no force is applied as shown at 904. As the garment is heated it transitions to austenite, causing contraction of the fabric. At first, this contraction does not cause any force to be applied, until the garment reaches the same circumference as the body part it covers at 906. Thereafter, if the garment may continue to apply some force as shown at 908.

Figure 10A:
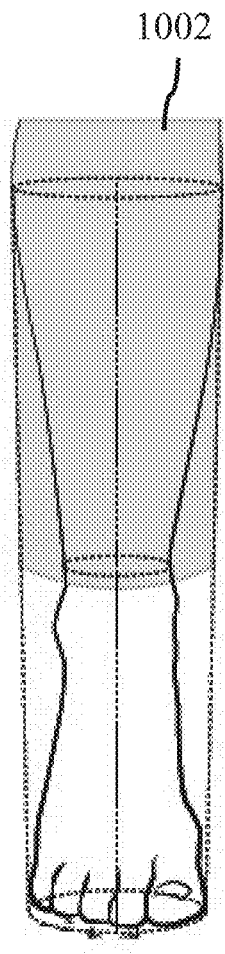
FIGS. 10A-10C depict three styles of garments having positive ease, zero ease, and negative ease, respectively.
Figure 10B:
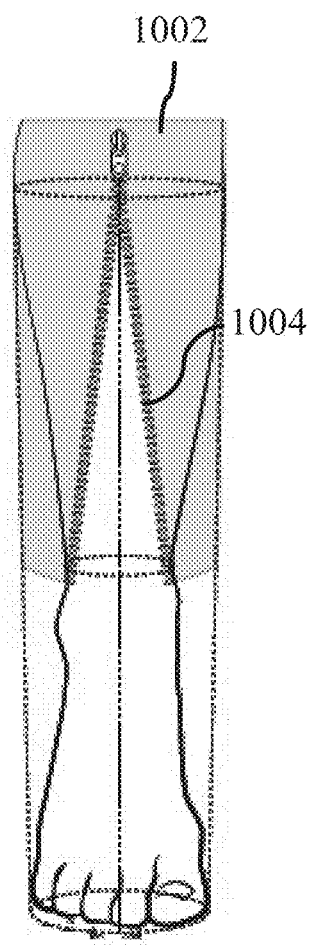
Figure 10C:
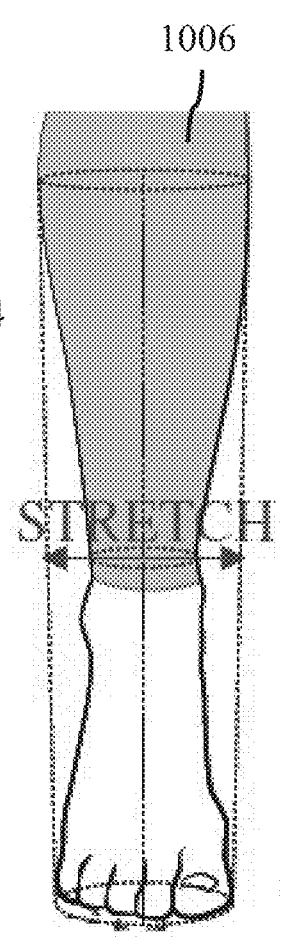

FIGS. 10A-10C depict three styles of garments that show the benefit of a self-fitting garment. An inelastic fabric garment such as garment 1002 shown in FIG. 10A is loose fitting, and leaves room between the leg and the garment 1002. An inelastic fabric garment 1004 of FIG. 10B can be made to be form fitting, but in order to be donned a fastener 1004 (here, a zipper) is required. In order to avoid the use of fastener 1004, a stretch fabric is used in garment 1006 to constrict the garment. For most wearers, the inelastic garment 1002 is the easiest to don or doff. Meanwhile, 1004 is the most appropriately sized for wearing, as it is neither constrictive nor baggy, but it suffers from the requirement of fasteners if it is made of an inelastic fabric. Forgoing the inelastic fabric of FIG. 10B and instead relying on elastic constriction of the elastic garment 1006 of FIG. 10C creates its own issues, such as overly constrictive garments and difficulty donning and doffing the garment 1006 as compared to an inelastic fabric such as those used in garments 1002 and 1004.

The required fit for various garments varies. For example, oversized t-shirts designed in three sizes may fit a larger portion of the population than a fitted dress shirt in six sizes due to the amount of garment ease that is aesthetically desired in that garment. In most garments that are not used for therapeutic compression, however, zero ease (or near to zero ease) is desirable for comfort and aesthetics.

Figure 11A:
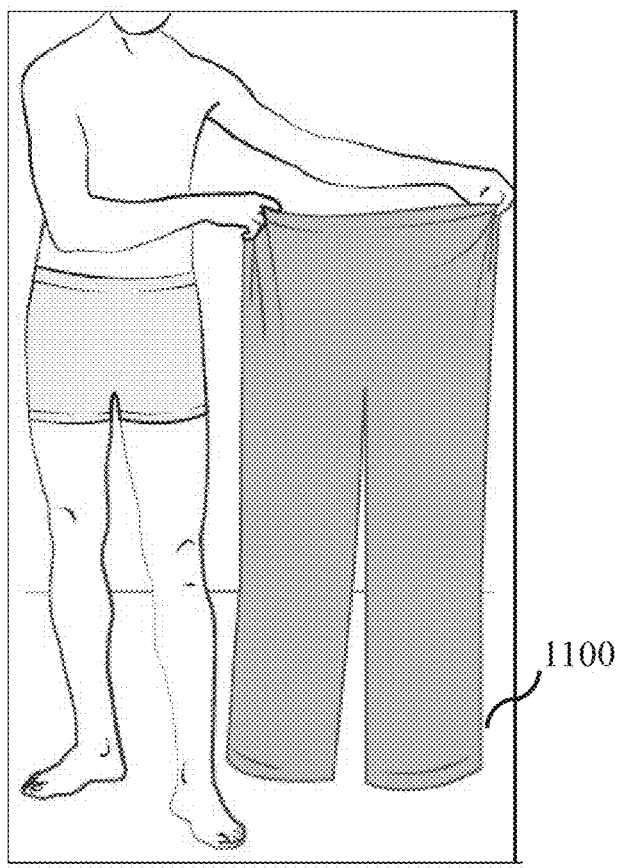
FIGS. 11A-11D depict a self-fitting garment that has approximately zero ease without the use of fasteners, according to an embodiment.
Figure 11B:
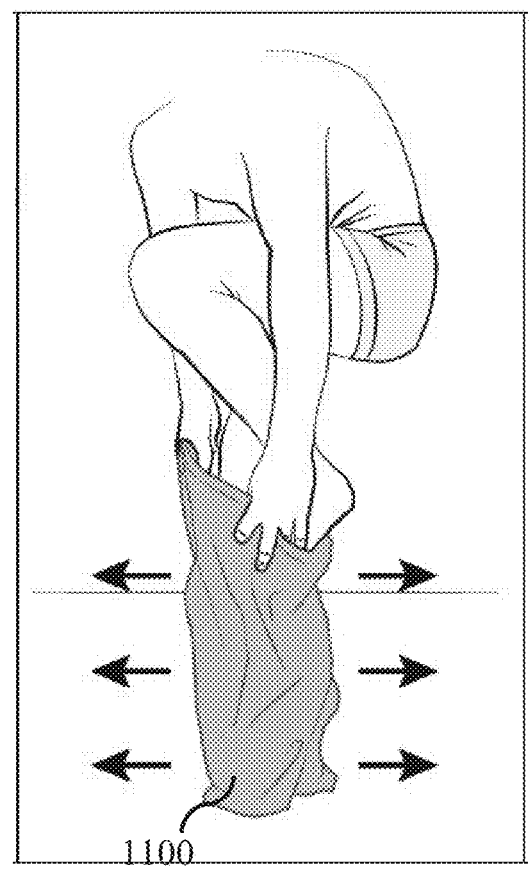
Figure 11C:
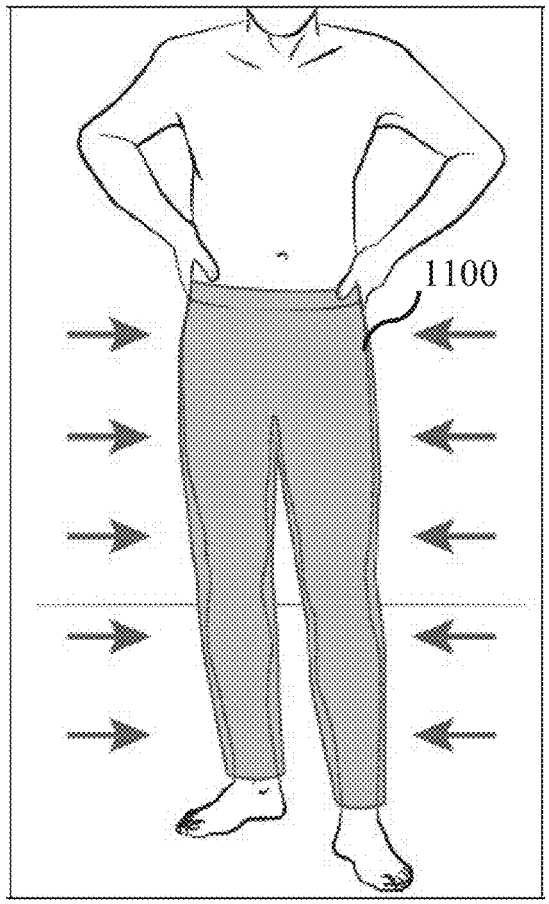
Figure 11D:
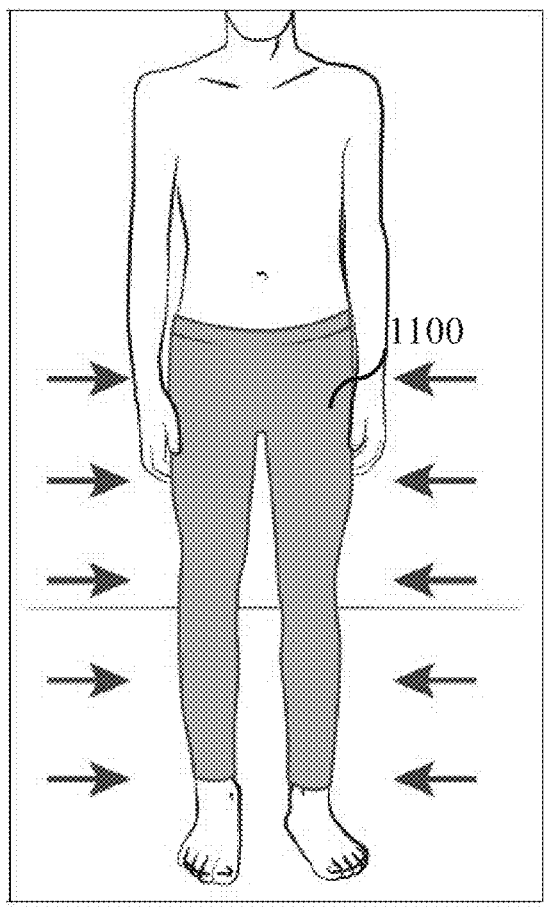
Figure 12:
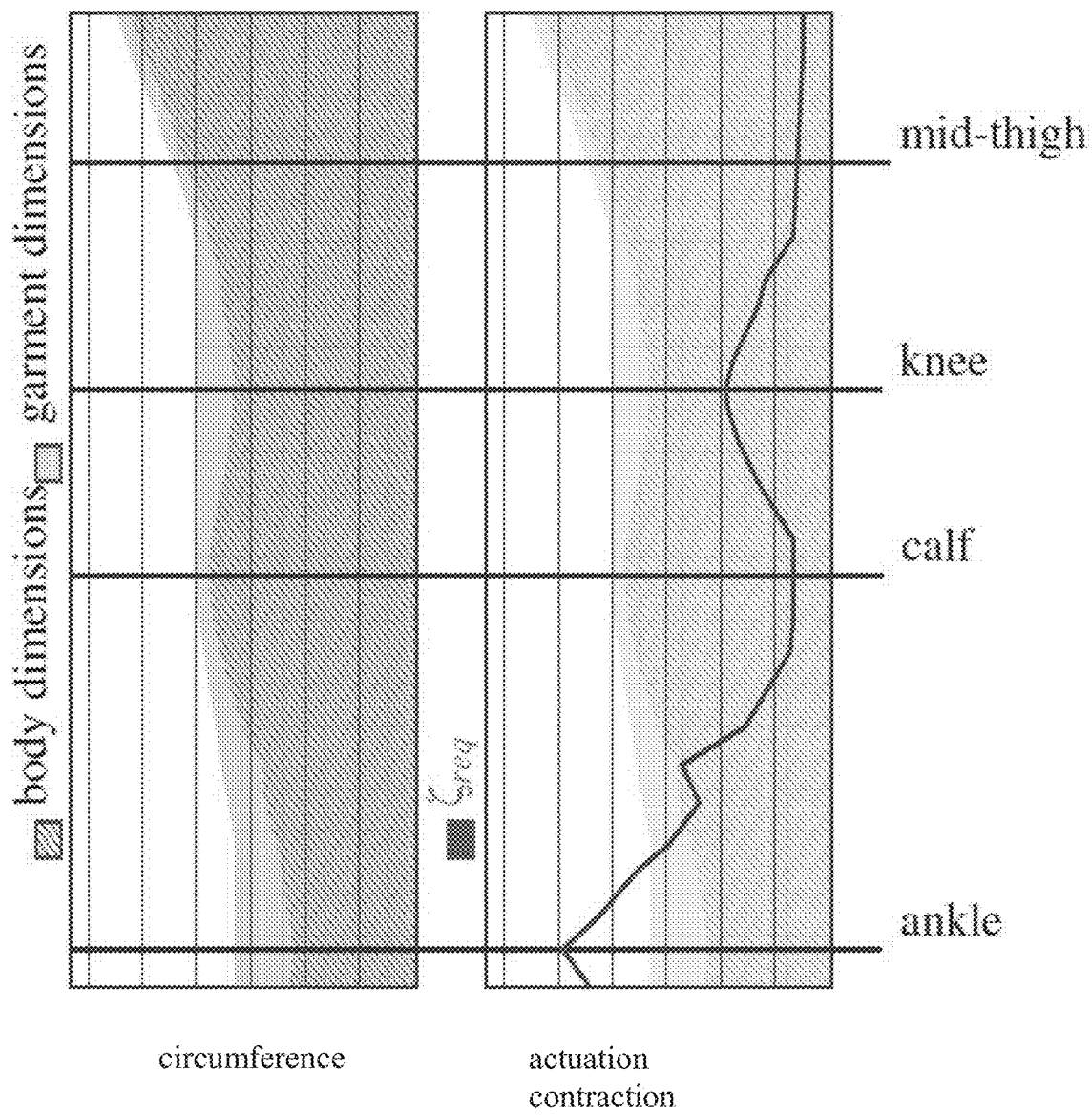
FIG. 12 depicts the required actuation contraction for a self-fitting garment according to an embodiment.

FIGS. 11A-11D depict a self-fitting garment that has approximately zero ease without the use of fasteners, according to an embodiment. As shown in FIG. 11A, the proposed garment 1100 is compliant and oversized before don (i.e., at stage 900 of FIG. 9). During the donning process, as shown in FIG. 11B the compliant garment 1100 is stretched out further as it is pulled over the limbs (i.e., at stage 902 of FIG. 9). Once on the body and free of external forces, the garment slightly relaxes around its new form as shown in FIG. 11C (i.e., at stage 904 of FIG. 9). The garment then warms to skin temperature, which causes the shape memory alloy materials that are knitted into garment 1100 to contract and stiffen as shown in FIG. 11D (i.e., to stage 906 and then 908 of FIG. 9). The result is a non-elastic, not stretchy garment with zero or near-zero ease. To doff, the garment would either need to be cooled or designed with release mechanisms.

Although garment 1100 is shown as a pair of pants, other garments can be made that will conform similarly. For each type of garment, a self-fitting garment can be designed by mapping the body-garment relationship. Contractile SMA knitted actuators exhibit tunable functional performance through the systematic modification of geometric design parameters, specifically wire diameter d and knit index $i_k$, as described above. Before determining suitable knit geometries to achieve self-fit, the body-garment relationship can be mapped. Mapping can be accomplished by gathering dimensional data from a sample group. Marks can be placed on the participants' body and at each incremental mark, a circumferential measurement is taken.

Once circumferential measurements have been gathered, the performance requirements of the self-fitting garment can be compared with the measurements to design a garment.

For an inextensible garment such as garment 1100, the minimum garment dimension required at the base of a pant leg to enable don/doff (i.e., traverse the foot) was determined to be the calf dimension plus 2.5 cm of positive ease. This recommended added garment dimension means that the garment circumference around the ankle should be equal to the garment dimension around the calf. Additionally, the garment 1100 dimension around the knee must be equal to the garment dimensions around the calf to enable the garment to traverse the calf. The required functional performance of the self-fitting garment is consequently defined as the percentual difference between the garment dimensions and the body dimensions. The circumference of the body and the garment are shown in the left-hand side of the graph in FIG. 12. Based on the initial and desired contracted circumference at each portion on the body (i.e., the initial length and contracted length of each circumferentially-extending shape memory coil), the required contraction $\zeta_{req}$ can be determined.

Figure 13:
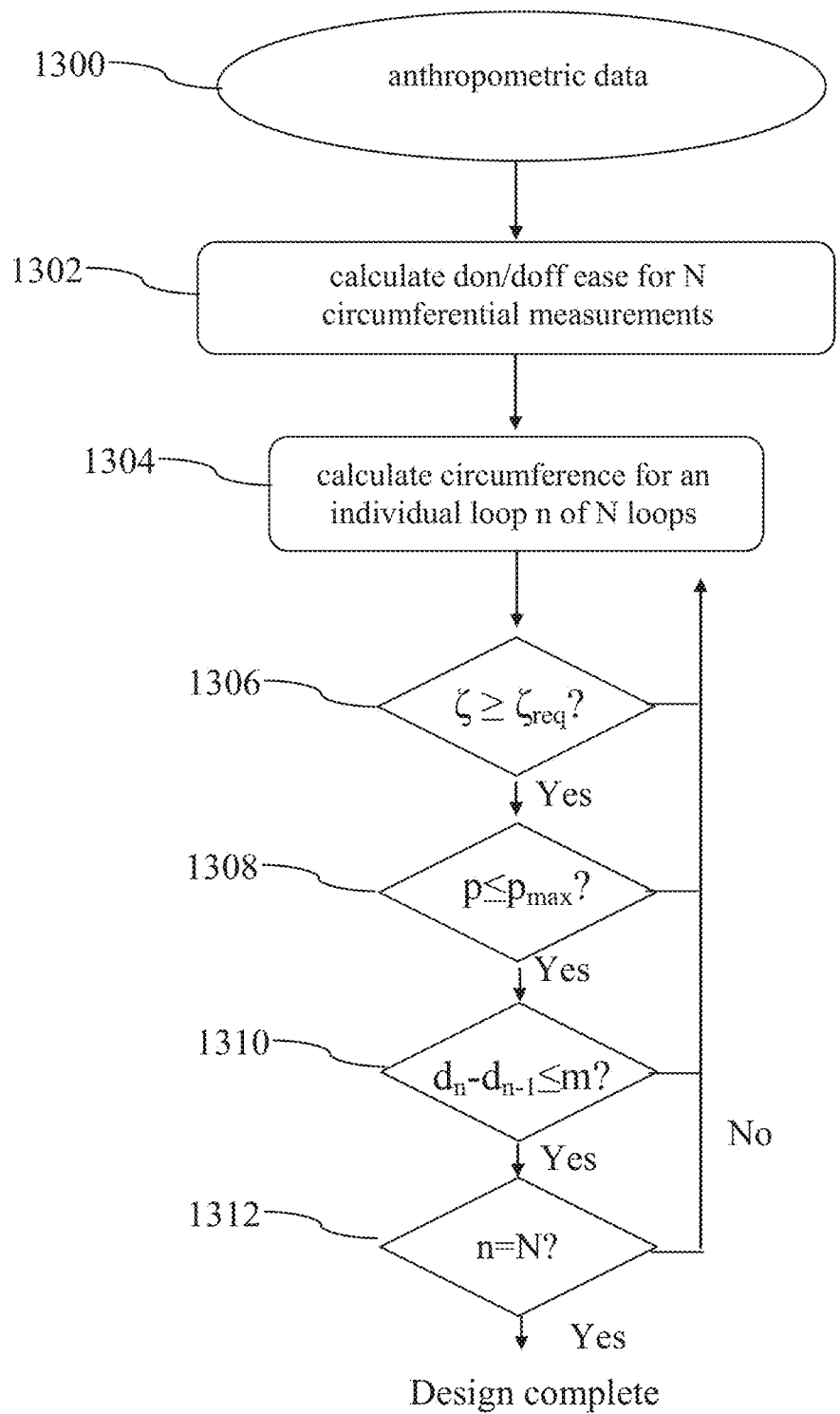
FIG. 13 illustrates a flowchart of a method for providing a self-fitting garment according to an embodiment.

For garments that are designed primary for comfort and aesthetics (i.e., where desired compression is near zero rather than a positive value), actuation contraction $\zeta_{req}$ should ordinarily be maximized while the force applied $F_{app}$ should be minimized, while still maintaining desired contraction under forces that are to be expected during wear. FIG. 13 shows a martensite-austenite transition loop corresponding to an embodiment. Upon donning the fully-martensitic garment at (1), small forces are exerted on the garment, which cause further garment dimensional expansion at (2). Upon release, the garment contracts into its martensite relaxed state and recovers some of the extension from the donning process (3). Heating (body or external source) causes the garment circumference to decrease to approximate the leg circumference at (4). Additional contractile ability of the garment results in a generation of forces and pressure on the leg, which are to be minimized in the design (though as described above with respect to therapeutic compression garments this may not always be the case).

FIG. 13 illustrates a flowchart of a method according to an embodiment. At 1300, anthropometric data is provided, such as from a database or from independent measurements of a body part for which a garment is being created. At 1302, the anthropometric data is used to calculate donning and doffing ease for N different body cross sections or circumferential measurements, as described above with respect to FIG. 12. At 1304, the ideal circumference for each of these N circumferential body cross-sections is determined. At 1306, for each body cross-sections n of the N total body cross-sections, an actuation contraction $\zeta$ is determined. If the actuation contraction $\zeta$ is too large (i.e., greater than the required actuation contraction $\zeta_{req}$), then the circumference for that knitted garment cross-section is recalculated (i.e. number of knit courses is added or subtracted) or another knitted architecture is selected. Otherwise, the pressure applied by that knitted architecture at a certain length (i.e. number of knitted courses) is calculated at 1308. The pressure applied by a knitted cross-section n is directly related to the force applied $F_{app}$. If the force is too great (e.g., more than 1333 Pa in some embodiments, or greater than 1000 Pa in other embodiments), then the circumference for that knitted cross-section is recalculated (i.e. number of knit courses is added or subtracted). Otherwise, the difference between the diameter of the wire used in knitted cross-section n and the diameter of the wire used in preceding knitted cross-section n−1 is determined. If that difference is greater than a threshold (e.g., 0.1 mm) then another knitted architecture is selected. Otherwise, the knitted architecture and the number of courses that make up that knitted cross-section n is finalized and the process is iterated through the remainder of the N cross-sections at 1312. Once all of the cross-sections from 1 to N are calculated, the design is complete.

FIGS. 14 and 15 show test data for a series of fabrics made with different knit indices and diameters.

Figure 14A:
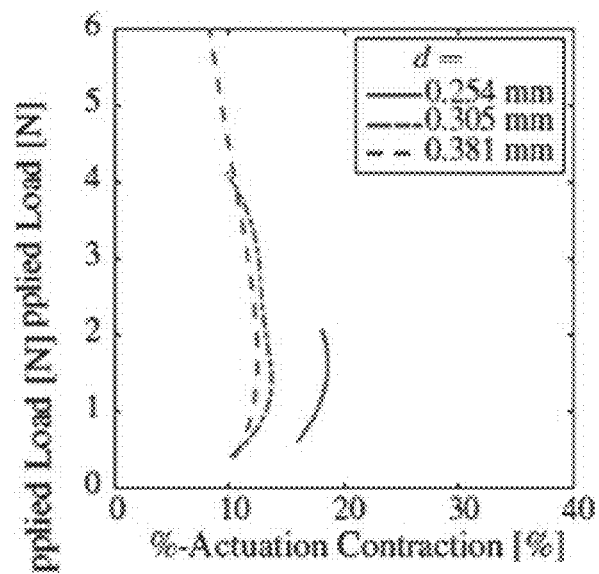
FIGS. 14A and 14B depict load, actuation contraction, and mechanical work in a self-fitting garment by materials having a common knit index.
Figure 14B:
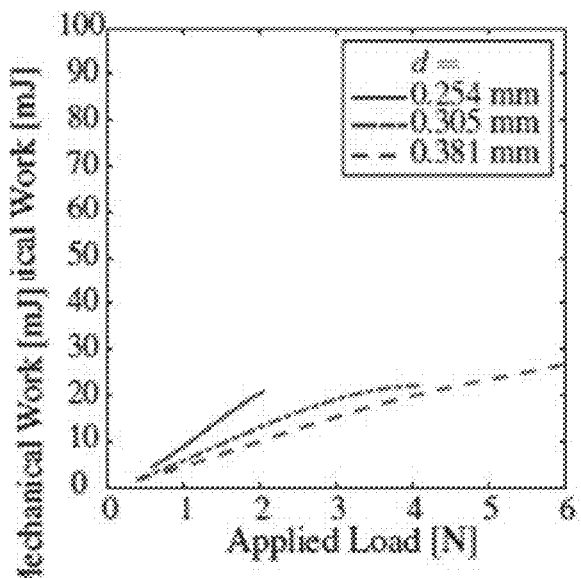

FIG. 14A shows applied load vs. actuation contraction for a series of loops of shape memory alloy material, all of which have a knit index of 65, but which have varying diameters. FIG. 14B shows mechanical work as a function of applied load for the same loops as FIG. 14A.

Figure 14C:
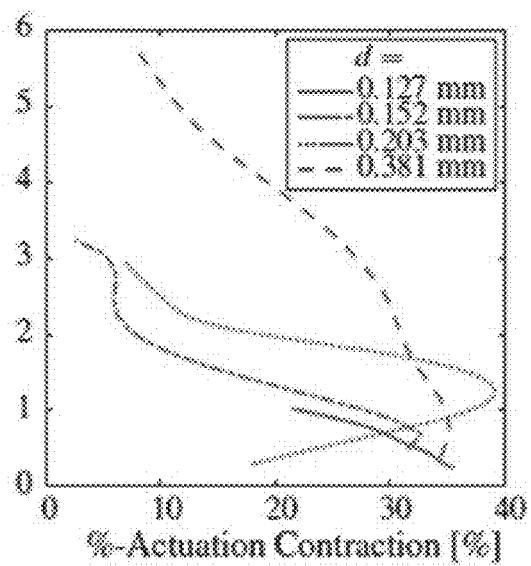
FIGS. 14C and 14D depict load, actuation contraction, and mechanical work in a self-fitting garment by materials having a second common knit index.
Figure 14D:
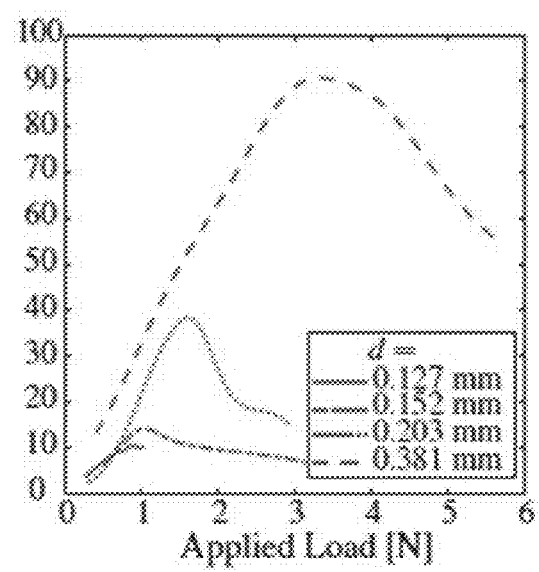

FIG. 14C shows applied load vs. actuation contraction for a series of loops of shape memory alloy material, all of which have a knit index of 130, but which have varying diameters. FIG. 14D shows mechanical work as a function of applied load for the same loops as FIG. 14C.

Figure 15A:
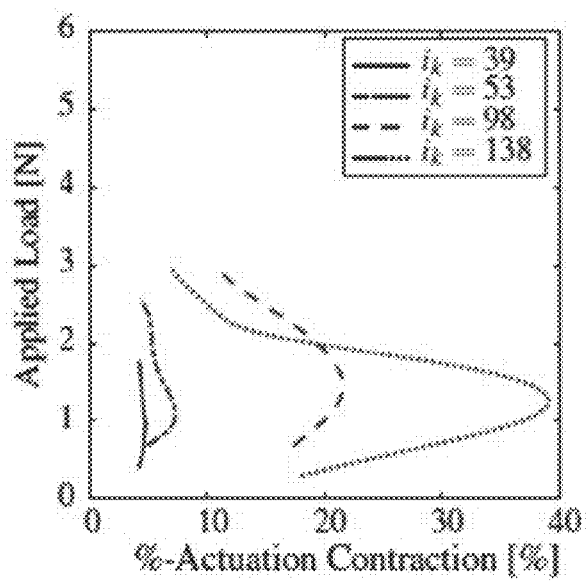
FIGS. 15A and 15B depict load, actuation contraction, and mechanical work in a self-fitting garment by materials having a common diameter and varying knit indices.
Figure 15B:
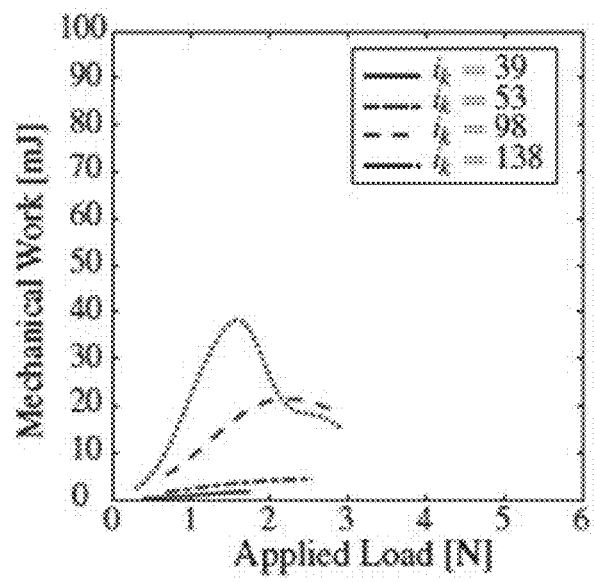

FIGS. 15A and 15B show applied load as a function of actuation contraction, and mechanical work as a function of applied load, respectively. Each of the lines depicted in FIGS. 15A and 15B corresponds to a shape memory coil having a diameter of 0.203 mm, but each of the lines has a different knit index, varying from 39 to 138. As shown in FIGS. 14A-14D and 15A-15B, a maximum actuation contraction point can be determined for each index and diameter. The maximum actuation contraction is a very useful and widely used metric for the analysis of the actuation performance of uniaxial actuators. The applied load over actuation contraction profiles of contractile SMA knitted actuators share the characteristic shape with a deflection point at the maximum actuation contraction. Under loading conditions below the maximum actuation contraction, the behavior of the knitted actuator is dominated by the variable stiffness upon phase transformation, which leverages the geometry to achieve constantly increasing actuation contractions. At applied loads larger than the force at maximum actuation contraction, the knitted architecture loses the ability to recover the deformations, which results in decreased actuation contractions. The maximum actuation contraction $\zeta$ is obtained by determining the global maxima of $(l_M-l_A)/l_M$, as described above.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A therapeutic garment configured to provide compression in a radial direction, the therapeutic garment comprising:
   a plurality of knitted rows of an active material each extending in an axial direction, each of the rows having a plurality of loops of the active material to define a knit index,
   wherein each of the plurality of loops of the active material defines a cross-sectional diameter, and
   wherein the knit index and the cross-sectional diameter are selected to provide a therapeutic level of applied force by the active material due to a thermal transition in the active material.

2. The therapeutic garment of claim 1 wherein the garment further comprises a plurality of knitted rows of a passive material that extend axially along the therapeutic garment.

3. The therapeutic garment of claim 1, further comprising a fastener.

4. The therapeutic garment of claim 1 wherein the therapeutic garment is a compression sock having an open end and a closed end, wherein the fibers extend along the axial direction between the open end and the closed end.

5. The therapeutic garment of claim 1 wherein the compression upon transition of the active material causes first level compression at a first portion along the axial direction and a second level of compression at a second portion along the axial direction, and wherein the first level of compression is different from the second level of compression.

6. The therapeutic garment of claim 5 wherein the first level of compression and the second level of compression are predetermined to provide a therapy.

7. The therapeutic garment of claim 1 wherein the active material is configured to provide pulsed pressure output.

8. The therapeutic garment of claim 1 wherein the active material is heated by an electrical power source.

9. The therapeutic garment of claim 1 wherein the active material has a transition temperature that is between a room temperature of about 20° C. and a skin temperature of about 30° C.

10. The therapeutic garment of claim 1 wherein the active material has a transition temperature that is between a freezer temperature of about −15° C. and a skin temperature of about 30° C.

* * * * *